United States Patent [19]

Nakajima

[11] Patent Number: 5,580,553
[45] Date of Patent: Dec. 3, 1996

[54] COSMETIC COMPOSITION CONTAINING ALKENYLSUCCINIC ACID ESTER OF SACCHARIDE

[75] Inventor: Tohru Nakajima, Sakai, Japan

[73] Assignee: Nippon Starch Chemical Co., Ltd., Osaka, Japan

[21] Appl. No.: 177,368

[22] Filed: Jan. 5, 1994

Related U.S. Application Data

[63] Continuation-in-part of Ser. No. 932,947, Aug. 21, 1992, abandoned.

[51] Int. Cl.$^6$ .......................... A61K 31/045; A61K 31/13
[52] U.S. Cl. .......................... 424/78.17; 514/23; 536/18.7; 536/102; 536/124
[58] Field of Search .................... 424/70, 78.03, 424/78.17; 514/772.1, 777, 778, 785, 23, 53, 54, 60, 61, 844; 536/110, 18.7, 102, 124

[56] References Cited

U.S. PATENT DOCUMENTS

| | | | |
|---|---|---|---|
| 2,613,206 | 10/1952 | Caldwell et al. | 536/110 |
| 2,661,349 | 12/1953 | Caldwell et al. | 536/110 |
| 2,868,781 | 1/1959 | Gaertner et al. | 536/110 |
| 2,891,947 | 6/1959 | Paschall et al. | 536/110 |
| 3,839,320 | 10/1974 | Bauer | 536/110 |
| 4,011,392 | 3/1977 | Rudolph et al. | 536/110 |
| 4,035,235 | 7/1977 | Richards et al. | 536/48 |
| 4,293,542 | 10/1981 | Lang et al. | 424/47 |
| 4,689,287 | 8/1987 | Katoh et al. | 430/230 |
| 4,711,669 | 12/1987 | Paul et al. | 106/204 |
| 4,765,922 | 8/1988 | Contamin et al. | . |
| 4,777,039 | 10/1988 | Lang et al. | 424/70 |
| 4,784,801 | 11/1988 | Hoeffkes et al. | . |
| 4,792,415 | 12/1988 | Colegrove | . |
| 5,064,555 | 11/1991 | Medcalf, Jr. et al. | . |

FOREIGN PATENT DOCUMENTS 691364   5/1953   United Kingdom .

*Primary Examiner*—Jeffrey C. Mullis
*Attorney, Agent, or Firm*—Foley & Lardner

[57] ABSTRACT

There is disclosed a cosmetic composition containing as an essential ingredient an alkenylsuccinic acid half ester of a saccharide which can be obtained by reacting the sugar with an alkenylsuccinic anhydride in the presence of an alkali catalyst.

9 Claims, No Drawings

COSMETIC COMPOSITION CONTAINING ALKENYLSUCCINIC ACID ESTER OF SACCHARIDE

This application is a continuation-in-part application of application Serial No. 07/932,947 filed Aug. 21, 1992, now abandoned.

FIELD OF THE INVENTION

The present invention relates to a cosmetic composition containing an alkenylsuccinic acid ester of a saccharide which has good affinity for hair and skin and provides good feeling upon use and good finish. Further, the cosmetic composition of the present invention is dermatologically stable.

BACKGROUND OF THE INVENTION

In recent years, natural products or their derivatives tend to be widely used as a base for cosmetics in view of their harmlessness to the human body, affinity for hair or skin and excellent properties. Examples thereof include polysaccharides such as hydrolyzed proteins, lanolin, lipids, vitamins, cellulose, guar gum, starch and their derivatives. For example, U.S. Pat. No. 3,186,911 discloses a composition for setting hair which contains aminated starch which is a tert-aminoalkyl ether of starch and is composed of 25 to 50% by weight of amylose and 75 to 50% by weight of amylopectin. Further, JP-B 47-20635 discloses the use of a water-soluble cationic nitrogen-containing polymer for shampoos and hair cosmetics.

These conventional raw materials have been used as protective colloids, thickening agents, film forming agents and the like. Since higher performances of cosmetics have been requested in recent years, cosmetics produced by using these conventional raw materials are unsatisfactory. For example, shampoos and hair cosmetics containing a cationic modified polymer provide moistness and softness upon washing and rinsing hair, but cause uncomfortable stickiness upon drying hair. Further, a complex of the cationic modified polymer and a surfactant solidifies and becomes stiff as it dries, and preferred hair touch after drying is not obtainable. Thus, these shampoos and hair cosmetics are unsatisfactory.

OBJECTS OF THE INVENTION

The main object of the present invention is to provide a cosmetic composition having good feeling upon use and good finish, which have been difficult to obtain in conventional cosmetics, using conventional raw materials and having dermatological stability.

This object as well as other objects and advantages of the present invention will become apparent to those skilled in the art from the following description.

SUMMARY OF THE INVENTION

The present inventors have intensively studied to attain the above object. As a result, it has been found that a cosmetic composition satisfying the above objective of the present invention can be produced by using a cosmetic base comprising an alkenylsuccinic acid half ester of a saccharide which can be obtained by reacting a saccharide with an alkenylsuccinic anhydride. Thus, the present invention has been completed.

That is, according to the present invention, there is provided a cosmetic composition comprising an alkenylsuccinic acid half ester of a saccharide. The half ester is obtained by reacting a saccharide with an alkenylsuccinic anhydride and may be its purified form or a reaction mixture.

DETAILED DESCRIPTION OF THE INVENTION

As the saccharide used as the starting material in the present invention, there can be used monosaccharides [e.g., aldopentose (e.g., ribose, arabinose, xylose, lyxose, etc), aldohexose (e.g., glucose, mannose, allose, altrose, talose, galactose, idose, gulose, etc.), ketopentose (e.g., ribulose, xylulose, etc.), ketohexose (e.g., fructose, psicose, sorbose, tagatose, etc.), rhamnose, etc.], oligosaccharides (e.g., sucrose, maltodextrins, cyclodextrins, isomaltodextrins, cellooligosaccharides, galactooligosaccharides, mannooligosaccharides, etc.), hydrolyzed starch (e.g., enzyme denatured dextrin, roasted dextrin, etc.), amino sugars (e.g., glucosamine, galactosamine (chondrosamine), mannosamine, gulosamine, kanosamine, etc.), acidic sugars (e.g., glucuronic acid, glulonic acid, galacturonic acid, mannuronic acid, etc.), sugar alcohol (e.g., glycerin, erythritol, ribitol, arabitol, mannitol, sorbitol (glucitol), dulcitol, volemitol, etc.), other sugars (e.g., saccharified materials of reduced starch (reduced starch syrup), reduced malt syrup and the like.

In the present invention, an alkenylsuccinic anhydride is reacted, as a reagent for esterification with the above sugar. Examples of the alkenylsuccinic anhydride include $C_{2-20}$ alkenyl-succinic anhydride, more preferably, $C_{8-18}$ alkenylsuccinic anhydride such as octenylsuccinic anhydride, decenylsuccinic anhydride, dodecenylsuccinic anhydride, tetradecenylsuccinic anhydride, hexadecenylsuccinic anhydride, octadecenylsuccinic anhydride and the like.

The esterification is carried out by dissolving the saccharide in water or a mixed solvent of water and an organic solvent (e.g., alcohol, acetone, etc.) and reacting the alkenylsuccinic anhydride in the presence of an alkali catalyst. The reaction is carried out with stirring at 10° to 50° C., while the pH is maintained at 6 to 9. Examples of the alkali catalyst include hydroxides of alkaline metals or alkaline earth metals (e.g., sodium hydroxide, potassium hydroxide, lithium hydroxide, etc.), carbonates of alkaline metals or alkaline earth metals (e.g., sodium carbonate, potassium carbonate, lithium carbonate, etc.), alkoxides of alkaline metals or alkaline earth metals (e.g., sodium methoxide, sodium ethoxide, potassium methoxide, etc.), ammonia, mono-, di- or trialkylamines having $C_{1-6}$ alkyl group(s) (e.g., methylamine, dimethylamine, trimethylamine, ethylamine, diethylamine, triethylamine, propylamine, dipropylamine, butylamine, isobutylamine, sec-butylamine, tert-butylamine, amylamine, sec-amylamine, tert-amylamine, hexylamine, etc), di- or trialcoholamine having hydroxyl group(s) (e.g., triethanolamine, triisopropanolamine, diethanolamine, etc.) and the like.

The alkenylsuccinic acid half ester of a saccharide of the present invention is a half ester of the saccharide formed by ring-opening reaction of the alkenylsuccinic anhydride with the above catalyst, followed by esterification with the saccharide. The other carboxyl group is neutralized with the catalyst used, and the ester is obtained as a solution of the salt with alkaline metals, alkaline earth metals or amines. The amount of the alkenylsuccinic anhydride to be added relative to the saccharide is at least 30 parts by weight based on 100 parts by weight of the saccharide. When the amount of the alkenylsuccinic anhydride is too small, foaming ability of a cosmetic product becomes insufficient. From the economical viewpoint, the amount of the alkenylsuccinic anhydride is preferably at most 150 parts by weight based on 100 parts by weight of the saccharide.

The alkenylsuccinic acid half ester of a saccharide to be used in the present invention may be a reaction mixture as it is or its purified form purified by a conventional purification method such as precipitation with a solvent (e.g., $C_{1-3}$ alcohol, acetone, ether, etc.). For convenient sake, it is preferable to used a reaction mixture as it is.

In the case that unreacted saccharide remains in the reaction mixture, conventional antiseptics or mildewproofing agents may be added. However, since the alkenylsuccinic acid half ester itself used in the present invention are antibacterial, when the addition of antiseptics or mildewproofing agents is undesirable, there is no need to use them.

The alkenylsuccinic acid half ester of a saccharide of the present invention is formulated into a cosmetic composition in the form of conventional cosmetic compositions such as hair care compositions, skin care compositions and dentifrice according to per se known methods. Other ingredients are not specifically limited and there can be used conventional cosmetic carrier, diluents, or excipients such as various surfactants, oily materials (e.g., long chain fatty acid esters, hydrocarbons, etc.), hydrolyzed proteins, lanolin, lipids, perfumes, pigments, hydrotrope and the like. Further, vitamins and other nutritionally or pharmacologically effective ingredients can be added.

When the alkenylsuccinic acid half ester of a saccharide of the present invention is formulated into a cosmetic composition for hair care such as shampoo, rinse or the like, the amount of the ester to be formulated is preferably 0.1 to 15% by weight based on the total weight of the composition. When it is lower than 0.1% by weight, a satisfactory effect cannot be obtained. On the other hand, when it exceeds 15% by weight, an undesirable touch is sometimes caused. When the ester is formulated into a cosmetic composition for skin care such as cream, the amount of the ester is preferably 0.5 to 30% by weight based on the total weight of the composition.

The cosmetic composition containing the alkenylsuccinic acid half ester of a saccharide of the present invention has the following advantages.

(1) The cosmetic composition has an excellent affinity for hair and skin, excellent film-forming properties and high absorptivity to them.

(2) The half ester can be used in combination with various surfactants without lowering of the effects of protective colloids.

(3) When the cosmetic composition is used as a shampoo, it provides stabilized foam and excellent sustained lathering.

(4) The cosmetic composition has excellent moisture retention, makes hair and skin moist, provides excellent elasticity to hair and improves gloss of hair. Further, these effects are sustained.

(5) Because the cosmetic composition provides smoothness to hair and skin, the touch after its use becomes smooth. When the cosmetic composition is used as a shampoo, one can run a comb through his hair smoothly without snarling of the hair. When the cosmetic is used as a cream, the appearance of the product is not marred, and it provides excellent feeling upon use and excellent finish.

(6) When the cosmetic composition is used as a dentifrice, the cleaning effect and a feeling at the use are improved.

(7) In the alkenylsuccinic acid half ester of a saccharide of the present invention, saccharides are used as the raw material. Therefore, the ester has excellent biodegradability.

The following examples further illustrate the present invention in detail, but are not to be construed to limit the scope thereof. In the examples, all "parts" are by weight unless otherwise stated.

EXAMPLE 1

Glucose (100 parts) was dissolved in water (80 parts) with heating. Octenylsuccinic anhydride (80 parts) was added. With stirring at 30° C., the mixture was adjusted to pH 7.5 with 20% sodium hydroxide solution, followed by reaction for 5 hours. After the reaction, the water content was adjusted and a 70% aqueous solution of the product (half ester) was prepared (Sample No. 1).

EXAMPLE 2

The product was obtained according to the same manner as that described in Example 1 except that triethanolamine was used as the catalyst for the pH adjustment (Sample No. 2). Since triethanolamine was used, the free carboxyl group derived from octenylsuccinic anhydride in the product formed a salt with triethanolamine salt. Therefore, the number of moles of hydroxy group of glucose which was substituted with octenylsuccinic anhydride per 1 mole of glucose in the product (MS) could be determined directly by titration of the triethanolamine salt with sodium hydroxide as follows.

A sample of the product (about 3 g) was weighed precisely and added thereto water (50 ml) and ether (50 ml). The mixture was warmed and vigorously shaken. After standing for 10 minutes, an aqueous phase was separated and concentrated to dryness with heating under reduced pressure. After cooling, the residue was weighed. Then, water (20 ml) was added to the dried sample and the residue was dissolved with warming. Ethenol (50 ml) was added thereto and the mixture was titrated with aqueous 0.1N sodium hydroxide to determine the amount of octenyulsuccinic ester group (mg) in the sample. Then, MS was calculated. As a result, MS of this product was 0.66.

EXAMPLE 3

The product was obtained according to the same manner as that described in Example 1 except that glycerin was used instead of glucose (Sample No. 3).

EXAMPLE 4

The product was obtained according to the same manner as that described in Example 1 except that glycerin was used instead of glucose and that triethanolamine was used as a catalyst for pH adjustment (Sample No. 4). MS of this product determined according to the same manner as Example 2 was 0.34.

EXAMPLE 5

The product was obtained according to the same manner as that described in Example 1 except that sorbitol was used instead of glucose (Sample No. 5).

EXAMPLE 6

The product was obtained according to the same manner as that described in Example 1 except that sorbitol was used instead of glucose and that triethanolamine was used as a catalyst for the pH adjustment (Sample No. 6). MS of this product determined according to the same manner as Example 2 was 0.67.

EXAMPLE 7

The product was obtained according to the same manner as that described in Example 1 except that enzyme denatured dextrin was used instead of glucose (Sample No. 7).

EXAMPLE 8

The product was obtained according to the same manner as that described in Example 1 except that enzyme denatured dextrin was used instead of glucose and that triethanolamine was used as a catalyst for the pH adjustment (Sample No. 8). MS of this product determined according to the same manner as Example 2 was 0.59.

EXAMPLE 9

Sorbitol (100 parts) was dissolved in water (80 parts) under heating. Octenylsuccinic anhydride (30 parts) was added. With stirring at 30° C., the mixture was adjusted to pH 7.5, followed by reaction for 5 hours. After the reaction, the water content was adjusted, and a 70% aqueous solution of the product was prepared (Sample No. 9). MS of this product determined according to the same manner as Example 2 was 0.25.

EXAMPLE 10

The product was obtained according to the same manner as that described in Example 9 except that the amount of octenylsuccinic anhydride to be added was 50 parts (Sample No. 10). MS of this product determined according to the same manner as Example 2 was 0.42.

EXAMPLE 11

The product was obtained according to the same manner as that described in Example 9 except that the amount of octenylsuccinic anhydride to be added was 150 parts (Sample No. 11). MS of this product determined according to the same manner as Example 2 was 1.25.

EXAMPLE 12

The product was obtained according to the same manner as that described in Example 10 except that dodecenylsuccinic anhydride was used instead of octenylsuccinic anhydride (Sample No. 12). MS of this product determined according to the same manner as Example 2 was 0.20.

EXAMPLE 13

The product was obtained according to the same manner as that described in Example 10 except that tetradecenylsuccinic anhydride was used instead of octenylsuccinic anhydride (Sample No. 13). MS of this product determined according to the same manner as Example 2 was 0.18.

EXAMPLE 14

The product was obtained according to the same manner as that described in Example 10 except that octadecenylsuccinic anhydride was used instead of octenylsuccinic anhydride (Sample No. 14). MS of this product determined according to the same manner as Example 2 was 0.15.

EXAMPLE 15

Fourteen alkenylsuccinic acid esters of sugars obtained in Example 1 to 14 were tested with regard to foaming ability and stability of foam of JIS K 3362-1990. The foaming ability was determined by measuring the height of foam generated when test solutions (each 200 ml) of a given concentration (0.05, 0.1, 0.2, 0.3, 0.4, 0.5, 1.0, 2.0%) were dropped on a liquid surface from the height of 900 mm at 30° C. over 30 minutes. The stability of foam was determined by measuring the height of foam after 5 minutes. For comparison, unmodified glucose, glycerin, sorbitol and enzyme denatured dextrin were also tested.

The results are shown in Table 1 and 2.

TABLE 1

| | Amount of foam immediately after the drop at a given concentration (mm) (= foaming ability) | | | | | | | |
|---|---|---|---|---|---|---|---|---|
| Sample | 0.05% | 0.1% | 0.2% | 0.3% | 0.4% | 0.5% | 1.0% | 2.0% |
| No. 1 | 37 | 57 | 105 | 140 | 168 | 180 | 236 | 243 |
| 2 | 39 | 59 | 104 | 143 | 171 | 193 | 255 | 261 |
| 3 | 30 | 60 | 98 | 138 | 101 | 194 | 248 | 256 |
| 4 | 31 | 62 | 101 | 141 | 108 | 205 | 264 | 271 |
| 5 | 35 | 56 | 101 | 146 | 170 | 194 | 245 | 281 |
| 6 | 37 | 58 | 108 | 149 | 175 | 206 | 257 | 290 |
| 7 | 34 | 57 | 110 | 131 | 167 | 175 | 241 | 243 |
| 8 | 37 | 60 | 114 | 135 | 170 | 183 | 248 | 250 |
| 9 | 12 | 31 | 62 | 118 | 131 | 149 | 161 | 170 |
| 10 | 30 | 46 | 72 | 125 | 142 | 164 | 178 | 195 |
| 11 | 43 | 52 | 91 | 119 | 158 | 163 | 213 | 230 |
| 12 | 37 | 40 | 54 | 81 | 94 | 127 | 192 | 214 |
| 13 | 25 | 38 | 49 | 79 | 89 | 116 | 181 | 195 |
| 14 | 23 | 36 | 50 | 76 | 86 | 113 | 179 | 187 |
| Glucose | 0 | 0 | 0 | 0 | 0 | 0 | 0 | 0 |
| Glycerin | 0 | 0 | 0 | 0 | 0 | 0 | 0 | 0 |
| Sorbitol | 0 | 0 | 0 | 0 | 0 | 0 | 0 | 0 |
| Enzyme denatured dextrin | 0 | 0 | 0 | 0 | 0 | 0 | 0 | 0 |

TABLE 2

| | Amount of foam after 5 minutes at a given concentration (mm) (= Stability of foam) | | | | | | | |
|---|---|---|---|---|---|---|---|---|
| Sample | 0.05% | 0.1% | 0.2% | 0.3% | 0.4% | 0.5% | 1.0% | 2.0% |
| No. 1 | 14 | 30 | 67 | 107 | 132 | 156 | 214 | 215 |
| 2 | 15 | 31 | 69 | 108 | 134 | 158 | 215 | 217 |
| 3 | 9 | 36 | 67 | 103 | 125 | 166 | 215 | 218 |
| 4 | 11 | 38 | 68 | 105 | 129 | 168 | 219 | 221 |
| 5 | 13 | 37 | 65 | 110 | 141 | 168 | 212 | 243 |
| 6 | 15 | 40 | 67 | 112 | 143 | 170 | 214 | 245 |
| 7 | 14 | 28 | 54 | 93 | 135 | 148 | 208 | 210 |
| 8 | 14 | 30 | 56 | 95 | 137 | 150 | 211 | 212 |
| 9 | 7 | 15 | 31 | 76 | 101 | 122 | 137 | 144 |
| 10 | 18 | 22 | 36 | 81 | 109 | 135 | 151 | 165 |
| 11 | 19 | 33 | 64 | 94 | 124 | 136 | 180 | 190 |
| 12 | 12 | 25 | 38 | 64 | 74 | 106 | 162 | 177 |
| 13 | 10 | 23 | 36 | 64 | 72 | 98 | 154 | 156 |
| 14 | 9 | 21 | 35 | 62 | 71 | 96 | 146 | 150 |
| Glucose | 0 | 0 | 0 | 0 | 0 | 0 | 0 | 0 |
| Glycerin | 0 | 0 | 0 | 0 | 0 | 0 | 0 | 0 |
| Sorbitol | 0 | 0 | 0 | 0 | 0 | 0 | 0 | 0 |

TABLE 2-continued

| Sample | \multicolumn{8}{c}{Amount of foam after 5 minutes at a given concentration (mm) (= Stability of foam)} |
|---|---|---|---|---|---|---|---|---|
| | 0.05% | 0.1% | 0.2% | 0.3% | 0.4% | 0.5% | 1.0% | 2.0% |
| Enzyme denatured dextrin | 0 | 0 | 0 | 0 | 0 | 0 | 0 | 0 |

EXAMPLE 16

Solutions (each 2%) of the 14 alkenylsuccinic acid esters of a sugar obtained in Example 1 to 14 and unmodified glucose, glycerin, sorbitol and enzyme denatured dextrin were prepared, and the emulsifying ability was determined as follows.

A sample solution (60 g) was placed in a 500 ml beaker and refined rapeseed oil (60 g) was added. The mixture was stirred for 1 minute at 9,000 rpm with a homomixer. Immediately after the stirring, the mixture was transferred into a 100 ml messcylinder, followed by adjustment to 100 ml. After 24 hours, the separated state of each phase was observed. The results are shown in Table 3.

TABLE 3

| Sample | Aqueous phase | Oil phase | Emulsion phase |
|---|---|---|---|
| No. 1 | 1 | 0 | 99 |
| 2 | 1 | 0 | 99 |
| 3 | 1 | 0 | 99 |
| 4 | 1 | 0 | 99 |
| 5 | 1 | 0 | 99 |
| 6 | 1 | 0 | 99 |
| 7 | 1 | 0 | 99 |
| 8 | 1 | 0 | 99 |
| 9 | 5 | 0 | 95 |
| 10 | 3 | 0 | 97 |
| 11 | 1 | 0 | 99 |
| 12 | 2 | 0 | 98 |
| 13 | 3 | 0 | 97 |
| 14 | 5 | 0 | 95 |
| Glucose | 54 | 46 | 0 |
| Glycerin | 57 | 43 | 0 |
| Sorbitol | 54 | 47 | 0 |
| Enzyme denatured dextrin | 41 | 57 | 2 |

EXAMPLE 17

Human patch test was carried out with the octenylsuccinic acid glucose ester triethanolamine (Sample No. 2).

As the subject, a total of 42 people (25 men and 17 women) aged 20 to 58 years were chosen.

By using a Fin Chamber (manufactured by EPITEST Ltd. Oy, imported and sold by Taishoh Seiyaku Kabushiki Kaisha), a 70% solution of the sample was applied occlusively to the brachial flexion side for 24 hours, followed by judgment. Namely, 24 hours after the application, the sample was removed. Thirty minutes after the removal and 24 hours after the removal, judgment was made by observing the state of the skin.

Judgment was made according to the following criteria.

−: No reaction (negative)

±: Slight erythema (negative)

+: Apparent erythema (positive)

++: Erythema and swelling, or erythema and papule (positive)

+++: vesicle other than the above (positive)

The results of the patch test for the 42 subjects are shown in Table 4 and 5.

The reaction at 30 minutes after the removal of sample (shown as judgment time of 24 hours in Table 4 and 5) was all (−) except that one subject was judged as (±). The reaction at 24 hours after the removal of sample (shown as judgment time of 48 hours in Table 4 and 5) was all (−), and no abnormalities were recognized. Further, at 7 days after the removal of sample, no abnormalities were recognized.

Thus, there is little possibility that the sample No. 2 causes sustained irritant reaction. The sample is regarded as a product which can be used safely.

TABLE 4

Results of the Patch Test

| No. | Subject | Sex[a] | Age | Judgment time (hours) | Judgment | Note (anamnesis) |
|---|---|---|---|---|---|---|
| 1 | S.A. | M | 55 | 24 | − | healthy |
| | | | | 48 | − | |
| 2 | I.I. | M | 58 | 24 | − | healthy |
| | | | | 48 | − | |
| 3 | E.I. | F | 30 | 24 | − | healthy |
| | | | | 48 | − | |
| 4 | A.K. | M | 39 | 24 | − | healthy |
| | | | | 48 | − | |
| 5 | Y.K. | M | 55 | 24 | − | healthy |
| | | | | 48 | − | |
| 6 | M.S. | F | 26 | 24 | ± | healthy |
| | | | | 48 | − | |
| 7 | I.S. | M | 29 | 24 | − | healthy |
| | | | | 48 | − | |
| 8 | H.D. | M | 32 | 24 | − | healthy |
| | | | | 48 | − | |
| 9 | J.T. | F | 29 | 24 | − | healthy |
| | | | | 48 | − | |
| 10 | H.T. | M | 56 | 24 | − | healthy |
| | | | | 48 | − | |
| 11 | T.N. | M | 29 | 24 | − | healthy |
| | | | | 48 | − | |
| 12 | T.M. | F | 54 | 24 | − | healthy |
| | | | | 48 | − | |
| 13 | S.Y. | M | 46 | 24 | − | healthy |
| | | | | 48 | − | |
| 14 | S.Y. | M | 37 | 24 | − | healthy |
| | | | | 48 | − | |
| 15 | I.W. | F | 20 | 24 | − | healthy |
| | | | | 48 | − | |
| 16 | K.A. | M | 20 | 24 | − | healthy |
| | | | | 48 | − | |
| 17 | R.A. | M | 20 | 24 | − | healthy |
| | | | | 48 | − | |
| 18 | J.A. | F | 20 | 24 | − | healthy |
| | | | | 48 | − | |
| 19 | T.I. | F | 20 | 24 | − | healthy |
| | | | | 48 | − | |
| 20 | T.O. | M | 20 | 24 | − | healthy |
| | | | | 48 | − | |
| 21 | Y.O. | M | 20 | 24 | − | healthy |
| | | | | 48 | | |

[a]M: male, F: female

TABLE 5

Results of the Patch Test

| No. | Subject | Sex[a] | Age | Judgment time (hours) | Judgment | Note (anamnesis) |
|---|---|---|---|---|---|---|
| 22 | R.K. | F | 20 | 24 | − | healthy |
|  |  |  |  | 48 | − |  |
| 23 | K.K. | F | 20 | 24 | − | healthy |
|  |  |  |  | 48 | − |  |
| 24 | N.K. | F | 20 | 24 | − | healthy |
|  |  |  |  | 48 | − |  |
| 25 | M.K. | M | 20 | 24 | − | healthy |
|  |  |  |  | 48 | − |  |
| 26 | K.K. | M | 20 | 24 | − | healthy |
|  |  |  |  | 48 | − |  |
| 27 | M.K. | F | 20 | 24 | − | healthy |
|  |  |  |  | 48 | − |  |
| 28 | A.K. | F | 20 | 24 | − | healthy |
|  |  |  |  | 48 | − |  |
| 29 | Y.S. | M | 20 | 24 | − | healthy |
|  |  |  |  | 48 | − |  |
| 30 | Y.S. | M | 20 | 24 | − | healthy |
|  |  |  |  | 48 | − |  |
| 31 | A.S. | M | 20 | 24 | − | healthy |
|  |  |  |  | 48 | − |  |
| 32 | S.S. | F | 20 | 24 | − | healthy |
|  |  |  |  | 48 | − |  |
| 33 | S.T. | M | 20 | 24 | − | healthy |
|  |  |  |  | 48 | − |  |
| 34 | M.T. | M | 20 | 24 | − | healthy |
|  |  |  |  | 48 | − |  |
| 35 | T.T. | M | 20 | 24 | − | healthy |
|  |  |  |  | 48 | − |  |
| 36 | N.T. | M | 20 | 24 | − | healthy |
|  |  |  |  | 48 | − |  |
| 37 | Y.M. | M | 20 | 24 | − | healthy |
|  |  |  |  | 48 | − |  |
| 38 | M.M. | F | 20 | 24 | − | healthy |
|  |  |  |  | 48 | − |  |
| 39 | J.M. | F | 20 | 24 | − | healthy |
|  |  |  |  | 48 | − |  |
| 40 | K.N. | F | 20 | 24 | − | healthy |
|  |  |  |  | 48 | − |  |
| 41 | K.N. | F | 20 | 24 | − | healthy |
|  |  |  |  | 48 | − |  |
| 42 | H.M. | M | 20 | 24 | − | healthy |
|  |  |  |  | 48 | − |  |

[a] M: male, F: female

EXAMPLE 18

Human patch test was carried out according to the same manner as that described in Example 17 except that the octenylsuccinic acid glycerin ester triethanolamine (Sample No. 4) obtained in Example 4 was used as the sample.

The results are shown in Table 6 and 7. The results are the same as those in Example 17 except that two subjects were judged as (±) in the reaction at 30 minutes after the removal of sample (shown as judgment time of 24 hours in Table 6 and 7).

TABLE 6

Results of the Patch Test

| No. | Subject | Sex[a] | Age | Judgment time (hours) | Judgment | Note (anamnesis) |
|---|---|---|---|---|---|---|
| 1 | S.A. | M | 55 | 24 | − | healthy |
|  |  |  |  | 48 | − |  |
| 2 | I.I. | M | 58 | 24 | − | healthy |
|  |  |  |  | 48 | − |  |
| 3 | E.I. | F | 30 | 24 | − | healthy |
|  |  |  |  | 48 | − |  |
| 4 | A.K. | M | 39 | 24 | − | healthy |
|  |  |  |  | 48 | − |  |
| 5 | Y.K. | M | 55 | 24 | − | healthy |
|  |  |  |  | 48 | − |  |
| 6 | M.S. | F | 26 | 24 | ± | healthy |
|  |  |  |  | 48 | − |  |
| 7 | I.S. | M | 29 | 24 | − | healthy |
|  |  |  |  | 48 | − |  |
| 8 | H.D. | M | 32 | 24 | − | healthy |
|  |  |  |  | 48 | − |  |
| 9 | J.T. | F | 29 | 24 | − | healthy |
|  |  |  |  | 48 | − |  |
| 10 | H.T. | M | 56 | 24 | − | healthy |
|  |  |  |  | 48 | − |  |
| 11 | T.N. | M | 29 | 24 | − | healthy |
|  |  |  |  | 48 | − |  |
| 12 | T.M. | F | 54 | 24 | − | healthy |
|  |  |  |  | 48 | − |  |
| 13 | S.Y. | M | 46 | 24 | − | healthy |
|  |  |  |  | 48 | − |  |
| 14 | S.Y. | M | 37 | 24 | − | healthy |
|  |  |  |  | 48 | − |  |
| 15 | I.W. | F | 20 | 24 | − | healthy |
|  |  |  |  | 48 | − |  |
| 16 | K.A. | M | 20 | 24 | − | healthy |
|  |  |  |  | 48 | − |  |
| 17 | R.A. | M | 20 | 24 | − | healthy |
|  |  |  |  | 48 | − |  |
| 18 | J.A. | F | 20 | 24 | − | healthy |
|  |  |  |  | 48 | − |  |
| 19 | T.I. | F | 20 | 24 | − | healthy |
|  |  |  |  | 48 | − |  |
| 20 | T.O. | M | 20 | 24 | − | healthy |
|  |  |  |  | 48 | − |  |
| 21 | Y.O. | M | 20 | 24 | − | healthy |
|  |  |  |  | 48 | − |  |

[a] M: male, F: female

TABLE 7

Results of the Patch Test

| No. | Subject | Sex[a] | Age | Judgment time (hours) | Judgment | Note (anamnesis) |
|---|---|---|---|---|---|---|
| 22 | R.K. | F | 20 | 24 | − | healthy |
|  |  |  |  | 48 | − |  |
| 23 | K.K. | F | 20 | 24 | − | healthy |
|  |  |  |  | 48 | − |  |
| 24 | N.K. | F | 20 | 24 | − | healthy |
|  |  |  |  | 48 | − |  |
| 25 | M.K. | M | 20 | 24 | − | healthy |
|  |  |  |  | 48 | − |  |
| 26 | K.K. | M | 20 | 24 | − | healthy |
|  |  |  |  | 48 | − |  |
| 27 | M.K. | F | 20 | 24 | − | healthy |
|  |  |  |  | 48 | − |  |
| 28 | A.K. | F | 20 | 24 | ± | healthy |
|  |  |  |  | 48 | − |  |
| 29 | Y.S. | M | 20 | 24 | − | healthy |
|  |  |  |  | 48 | − |  |
| 30 | Y.S. | M | 20 | 24 | − | healthy |
|  |  |  |  | 48 | − |  |
| 31 | A.S. | M | 20 | 24 | − | healthy |
|  |  |  |  | 48 | − |  |
| 32 | S.S. | F | 20 | 24 | − | healthy |
|  |  |  |  | 48 | − |  |

TABLE 7-continued

Results of the Patch Test

| No. | Subject | Sex[a] | Age | Judgment time (hours) | Judgment | Note (anamnesis) |
|---|---|---|---|---|---|---|
| 33 | S.T. | M | 20 | 24 | – | healthy |
|  |  |  |  | 48 | – |  |
| 34 | M.T. | M | 20 | 24 | – | healthy |
|  |  |  |  | 48 | – |  |
| 35 | T.T. | M | 20 | 24 | – | healthy |
|  |  |  |  | 48 | – |  |
| 36 | N.T. | M | 20 | 24 | – | healthy |
|  |  |  |  | 48 | – |  |
| 37 | Y.M. | M | 20 | 24 | – | healthy |
|  |  |  |  | 48 | – |  |
| 38 | M.M. | F | 20 | 24 | – | healthy |
|  |  |  |  | 48 | – |  |
| 39 | J.M. | F | 20 | 24 | – | healthy |
|  |  |  |  | 48 | – |  |
| 40 | K.N. | F | 20 | 24 | – | healthy |
|  |  |  |  | 48 | – |  |
| 41 | K.N. | F | 20 | 24 | – | healthy |
|  |  |  |  | 48 | – |  |
| 42 | H.M. | M | 20 | 24 | – | healthy |
|  |  |  |  | 48 |  |  |

[a]M: male, F: female

EXAMPLE 19

Human patch test was carried out according to the same manner as that described in Example 17 except that the octenylsuccinic acid dextrin ester triethanolamine (Sample No. 8) obtained in Example 8 was used as the sample.

The results are shown in Table 8 and 9 and are the same as those in Example 17.

TABLE 8

Results of the Patch Test

| No. | Subject | Sex[a] | Age | Judgment time (hours) | Judgment | Note (anamnesis) |
|---|---|---|---|---|---|---|
| 1 | S.A. | M | 55 | 24 | – | healthy |
|  |  |  |  | 48 | – |  |
| 2 | I.I. | M | 58 | 24 | – | healthy |
|  |  |  |  | 48 | – |  |
| 3 | E.I. | F | 30 | 24 | – | healthy |
|  |  |  |  | 48 | – |  |
| 4 | A.K. | M | 39 | 24 | – | healthy |
|  |  |  |  | 48 | – |  |
| 5 | Y.K. | M | 55 | 24 | – | healthy |
|  |  |  |  | 48 | – |  |
| 6 | M.S. | F | 26 | 24 | ± | healthy |
|  |  |  |  | 48 | – |  |
| 7 | I.S. | M | 29 | 24 | – | healthy |
|  |  |  |  | 48 | – |  |
| 8 | H.D. | M | 32 | 24 | – | healthy |
|  |  |  |  | 48 | – |  |
| 9 | J.T. | F | 29 | 24 | – | healthy |
|  |  |  |  | 48 | – |  |
| 10 | H.T. | M | 56 | 24 | – | healthy |
|  |  |  |  | 48 | – |  |
| 11 | T.N. | M | 29 | 24 | – | healthy |
|  |  |  |  | 48 | – |  |
| 12 | T.M. | F | 54 | 24 | – | healthy |
|  |  |  |  | 48 | – |  |
| 13 | S.Y. | M | 46 | 24 | – | healthy |
|  |  |  |  | 48 | – |  |
| 14 | S.Y. | M | 37 | 24 | – | healthy |
|  |  |  |  | 48 | – |  |
| 15 | I.W. | F | 20 | 24 | – | healthy |
|  |  |  |  | 48 | – |  |

TABLE 8-continued

Results of the Patch Test

| No. | Subject | Sex[a] | Age | Judgment time (hours) | Judgment | Note (anamnesis) |
|---|---|---|---|---|---|---|
| 16 | K.A. | M | 20 | 24 | – | healthy |
|  |  |  |  | 48 | – |  |
| 17 | R.A. | M | 20 | 24 | – | healthy |
|  |  |  |  | 48 | – |  |
| 18 | J.A. | F | 20 | 24 | – | healthy |
|  |  |  |  | 48 | – |  |
| 19 | T.I. | F | 20 | 24 | – | healthy |
|  |  |  |  | 48 | – |  |
| 20 | T.O. | M | 20 | 24 | – | healthy |
|  |  |  |  | 48 | – |  |
| 21 | Y.O. | M | 20 | 24 | – | healthy |
|  |  |  |  | 48 |  |  |

[a]M: male, F: female

TABLE 9

Results of the Patch Test

| No. | Subject | Sex[a] | Age | Judgment time (hours) | Judgment | Note (anamnesis) |
|---|---|---|---|---|---|---|
| 22 | R.K. | F | 20 | 24 | – | healthy |
|  |  |  |  | 48 | – |  |
| 23 | K.K. | F | 20 | 24 | – | healthy |
|  |  |  |  | 48 | – |  |
| 24 | N.K. | F | 20 | 24 | – | healthy |
|  |  |  |  | 48 | – |  |
| 25 | M.K. | M | 20 | 24 | – | healthy |
|  |  |  |  | 48 | – |  |
| 26 | K.K. | M | 20 | 24 | – | healthy |
|  |  |  |  | 48 | – |  |
| 27 | M.K. | F | 20 | 24 | – | healthy |
|  |  |  |  | 48 | – |  |
| 28 | A.K. | F | 20 | 24 | – | healthy |
|  |  |  |  | 48 | – |  |
| 29 | Y.S. | M | 20 | 24 | – | healthy |
|  |  |  |  | 48 | – |  |
| 30 | Y.S. | M | 20 | 24 | – | healthy |
|  |  |  |  | 48 | – |  |
| 31 | A.S. | M | 20 | 24 | – | healthy |
|  |  |  |  | 48 | – |  |
| 32 | S.S. | F | 20 | 24 | – | healthy |
|  |  |  |  | 48 | – |  |
| 33 | S.T. | M | 20 | 24 | – | healthy |
|  |  |  |  | 48 | – |  |
| 34 | M.T. | M | 20 | 24 | – | healthy |
|  |  |  |  | 48 | – |  |
| 35 | T.T. | M | 20 | 24 | – | healthy |
|  |  |  |  | 48 | – |  |
| 36 | N.T. | M | 20 | 24 | – | healthy |
|  |  |  |  | 48 | – |  |
| 37 | Y.M. | M | 20 | 24 | – | healthy |
|  |  |  |  | 48 | – |  |
| 38 | M.M. | F | 20 | 24 | – | healthy |
|  |  |  |  | 48 | – |  |
| 39 | J.M. | F | 20 | 24 | – | healthy |
|  |  |  |  | 48 | – |  |
| 40 | K.N. | F | 20 | 24 | – | healthy |
|  |  |  |  | 48 | – |  |
| 41 | K.N. | F | 20 | 24 | – | healthy |
|  |  |  |  | 48 | – |  |
| 42 | H.M. | M | 20 | 24 | – | healthy |
|  |  |  |  | 48 |  |  |

[a]M: male, F: female

EXAMPLE 20

Skin primary irritant test was carried out according to U.S. EPA guidelines (TSCA, Health Effect Test Guidelines;

Section HG "Primary Eye Irritation") by using the octenylsuccinic acid dextrin ester triethanolamine (Sample No. 8) obtained in Example 8 as the sample. The method and criteria were as follows.

Six rabbits (species: New Zealand White) were used per group. A 70% aqueous solution (0.5 ml) of the sample was applied to a gauze patch, which was pasted occlusively for 4.5 hours on a part where wool was sheared. After the removal of the patch, the sample was wiped off. Observation was made after 1 hour, 24 hours, 48 hours and 72 hours.

The criteria was according to the skin irritation evaluation score of Draize.

The results are shown below.

The total of points after 24 hours and 72 hours: 7

Skin primary irritant index: 0.6

Classification of irritation: Slightly irritant substance

EXAMPLE 21

Eye primary irritant test was carried out according to U.S. EPA guidelines (TSCA, Health Effect Test Guidelines; Section HG "Primary Eye Irritation") by using the octenylsuccinic acid dextrin ester triethanolamine (Sample No. 8) obtained in Example 8 as the sample. The method and criteria were as follows.

Six rabbits (species: New Zealand White) were used per group. Seventy percent aqueous solution (0.1 ml) of the sample was administered into the lower eyelid. Observation was made after 1 hour, 24 hours, 48 hours, 72 hours and 7 days.

The criteria was according to the eye irritation evaluation score of Draize.

The results are shown below.

Mean point in the maximum point group: 44.0 (after 72 hours)

Mean group point at 7 days: 8.0

Classification of irritation: Medium irritant substance (scale 5 of 1 to 8)

EXAMPLE 22

Eye primary irritant test was carried out according to the same manner as that described in Example 21 except that the concentration of the aqueous solution of the sample was 10% instead of 70%.

The results are shown below.

Mean point in the maximum point group: 9.3 (after 1 hour)

Mean group point after 48 hours: 0 (evaluation of sustainment)

Classification of irritation: Minimum irritation (scale 3 of 1 to 8)

EXAMPLE 23

A transparent shampoo of the formulation composition A shown in Table 10 was prepared by using 6 alkenylsuccinic acid esters of sugars of the sample No. 1, 3, 5, 7, 10 and 12. For comparison, a shampoo of the composition B containing no alkenylsuccinic acid esters of sugars was also prepared.

TABLE 10

| Composition | Amount of formulation (% by weight) | |
|---|---|---|
| | A | B |
| Sodium alkyl ether sulfate | 10 | 16 |
| Lauric acid diethanol amide | 3 | 4 |
| Alkenylsuccinic acid ester of sugar | 8 | 0 |
| Propylene glycol | 2 | 2 |
| Antiseptic, Pigment, Perfume | trace | trace |
| Purified water | balance | balance |

The shampoo was used by 15 female subjects for evaluation of the performance. The results are shown in Table 11. The value in Table 11 shows the remainder when the number of persons who judged that B is better was subtracted from the number of persons who judged that A is better.

TABLE 11

| Item | Shampoo[b] | | | | | |
|---|---|---|---|---|---|---|
| | 1 | 3 | 5 | 7 | 10 | 12 |
| At use: | | | | | | |
| Lathering | 10 | 11 | 13 | 9 | 8 | 11 |
| Sliminess | 10 | 10 | 11 | 11 | 11 | 12 |
| Smoothness | 11 | 11 | 12 | 13 | 11 | 11 |
| Running of a comb | 12 | 11 | 11 | 12 | 11 | 12 |
| After use: | | | | | | |
| Soft | 11 | 11 | 11 | 12 | 12 | 12 |
| Smoothness | 12 | 12 | 12 | 12 | 12 | 11 |
| Absence of stickiness | 10 | 10 | 10 | 9 | 9 | 9 |
| Running of a comb | 12 | 12 | 12 | 12 | 12 | 11 |
| Gloss | 13 | 13 | 13 | 13 | 13 | 13 |
| Taste | 13 | 13 | 13 | 13 | 13 | 12 |

[b] The numbers correspond to sample numbers of alkenylsuccinic acid esters of sugars

EXAMPLE 24

A cream shampoo (pearl) of the formulation composition A shown in Table 12 was prepared by using 6 alkenylsuccinic acid esters of sugars of the sample No. 2, 4, 6, 8, 10 and 12. For comparison, a shampoo of the composition B containing no alkenylsuccinic acid esters of sugars was also prepared.

TABLE 12

| Composition | Amount of formulation (% by weight) | |
|---|---|---|
| | A | B |
| Alkylsulfate triethanolamine salt | 10 | 15 |
| Coconut oil fatty acid monoethanolamide | 3 | 5 |
| Alkenylsuccinic acid ester of sugar | 8 | 0 |
| Ethylene glycol monostearate | 2 | 2 |
| Antiseptic, Pigment, Perfume | trace | trace |
| Purified water | balance | balance |

The shampoo was used by 15 female subjects for evaluation of the performance. The results are shown in Table 13. The value in Table 13 shows the remainder when the number of persons who judged that B is better was subtracted from the number of persons who judged that A is better.

TABLE 13

| Item | Shampoo[b] | | | | | |
|---|---|---|---|---|---|---|
| | 2 | 4 | 6 | 8 | 10 | 12 |
| At use: | | | | | | |
| Lathering | 10 | 10 | 13 | 9 | 8 | 12 |
| Sliminess | 10 | 11 | 12 | 11 | 11 | 11 |
| Smoothness | 11 | 11 | 12 | 13 | 11 | 12 |
| Running of a comb | 12 | 12 | 11 | 11 | 11 | 12 |
| After use: | | | | | | |
| Soft | 11 | 11 | 11 | 12 | 12 | 11 |
| Smoothness | 12 | 13 | 12 | 12 | 12 | 11 |
| Absence of stickiness | 10 | 10 | 9 | 10 | 9 | 10 |
| Running of a comb | 12 | 12 | 11 | 11 | 12 | 11 |
| Gloss | 13 | 13 | 13 | 12 | 13 | 13 |
| Taste | 13 | 13 | 13 | 13 | 13 | 12 |

[b]The numbers correspond to sample numbers of alkenylsuccinic acid esters of sugars

EXAMPLE 25

A shampoo for dandruff removal of the formulation composition A shown in Table 14 was prepared by using 6 alkenylsuccinic acid esters of sugars of the sample No. 2, 4, 6, 8, 10 and 12. For comparison, a shampoo of the composition B containing no alkenylsuccinic acid esters of sugars was also prepared.

TABLE 14

| Composition | Amount of formulation (% by weight) | |
|---|---|---|
| | A | B |
| Alkylsulfate triethanolamine salt | 12 | 16 |
| Luric acid diethanolamide | 2 | 3 |
| Alkenylsuccinic acid ester of sugar | 5 | 0 |
| Polyacrylic acid triethanolamine salt | 0.5 | 0.5 |
| Zinc piridinium-1-thiol-N-oxide | 1 | 1 |
| Pigment, Perfume | trace | trace |
| Purified water | balance | balance |

The shampoo was used by 15 female subjects for evaluation of the performance. The results are shown in Table 15. The value in Table 15 shows the remainder when the number of persons who judged that B is better was subtracted from the number of persons who judged that A is better.

TABLE 15

| Item | Shampoo[b] | | | | | |
|---|---|---|---|---|---|---|
| | 2 | 4 | 6 | 8 | 10 | 12 |
| At use: | | | | | | |
| Lathering | 10 | 11 | 13 | 12 | 9 | 11 |
| Sliminess | 10 | 11 | 12 | 13 | 12 | 12 |
| Smoothness | 11 | 11 | 12 | 11 | 11 | 12 |

TABLE 15-continued

| Item | Shampoo[b] | | | | | |
|---|---|---|---|---|---|---|
| | 2 | 4 | 6 | 8 | 10 | 12 |
| Running of a comb | 12 | 12 | 12 | 11 | 11 | 12 |
| After use: | | | | | | |
| Soft | 10 | 10 | 11 | 11 | 11 | 12 |
| Smoothness | 11 | 11 | 12 | 12 | 11 | 11 |
| Absence of stickiness | 12 | 12 | 12 | 12 | 12 | 11 |
| Running of a comb | 13 | 12 | 13 | 12 | 13 | 12 |
| Gloss | 13 | 12 | 12 | 11 | 12 | 12 |
| Taste | 13 | 13 | 13 | 13 | 13 | 13 |

[b]The numbers correspond to sample numbers of alkenylsuccinic acid esters of sugars

EXAMPLE 26

A cream rinse shown in Table 16 was prepared by using 6 alkenylsuccinic acid esters of sugars of the sample No. 1, 3, 5, 7, 10 and 12. For comparison, a rinse of the composition B containing no alkenylsuccinic acid esters of sugars was also prepared.

TABLE 16

| Composition | Amount of formulation (% by weight) | |
|---|---|---|
| | A | B |
| Stearyltrimethylammonium chloride | 1.0 | 1.5 |
| Alkenylsuccinic acid ester of sugar | 1.0 | 0 |
| Cetanol | 2.0 | 2.0 |
| 2-Octyldodecanol | 1.0 | 1.0 |
| Cationic cellulose | 0.5 | 0.5 |
| Polyoxyethylene cetyl ether | 1.0 | 1.0 |
| Propylene glycol | 5.0 | 5.0 |
| Methylparaben | 0.1 | 0.1 |
| Perfume | 0.2 | 0.2 |
| Purified water | balance | balance |

The rinse was used by 15 female subjects for evaluation of the performance. The results are shown in Table 17. The value in Table 17 shows the remainder when the number of persons who judged that B is better was subtracted from the number of persons who judged that A is better.

TABLE 17

| Item | Rinse[b] | | | | | |
|---|---|---|---|---|---|---|
| | 1 | 3 | 5 | 7 | 10 | 12 |
| At use: | | | | | | |
| Sliminess | 12 | 12 | 13 | 12 | 13 | 12 |
| Smoothness | 11 | 11 | 12 | 12 | 12 | 12 |
| Running of a comb | 12 | 12 | 13 | 13 | 13 | 13 |
| After use: | | | | | | |
| Soft | 10 | 11 | 11 | 11 | 12 | 12 |
| Smoothness | 11 | 11 | 12 | 12 | 12 | 12 |
| Absence of stickiness | 12 | 12 | 12 | 12 | 12 | 12 |
| Running of a comb | 13 | 13 | 13 | 13 | 13 | 13 |
| Gloss | 13 | 13 | 13 | 13 | 13 | 13 |
| Taste | 13 | 13 | 13 | 13 | 13 | 13 |

[b]The numbers correspond to sample numbers of alkenylsuccinic acid esters of sugars

EXAMPLE 27

An oil rinse shown in Table 18 was prepared by using 6 alkenylsuccinic acid esters of sugars of the sample No. 2, 4, 6, 8, 10 and 12. For comparison, a rinse of the composition B containing no alkenylsuccinic acid esters of sugars was also prepared.

TABLE 18

| Composition | Amount of formulation (% by weight) | |
|---|---|---|
| | A | B |
| Stearyltrimethylammonium chloride | 1.5 | 2.0 |
| Alkenylsuccinic acid ester of sugar | 1.0 | 0 |
| Polyoxyethylene cetyl ether | 1.0 | 1.0 |
| Polyoxyethylene lanolin ether | 3.0 | 3.0 |
| Propylene glycol | 5.0 | 5.0 |
| Citric acid | 0.1 | 0.1 |
| Sodium citrate | 0.15 | 0.15 |
| Butyl para-hydroxybenzoate | 0.05 | 0.05 |
| Methyl para-hydroxybenzoate | 0.1 | 0.1 |
| Perfume | 0.2 | 0.2 |
| Purified water | balance | balance |

The rinse was used by 15 female subjects for evaluation of the performance. The results are shown in Table 19. The value in Table 19 shows the remainder when the number of persons who judged that B is better was subtracted from the number of persons who judged that A is better.

TABLE 19

| Item | Rinse[b] | | | | | |
|---|---|---|---|---|---|---|
| | 2 | 4 | 6 | 8 | 10 | 12 |
| At use: | | | | | | |
| Sliminess | 12 | 12 | 13 | 12 | 13 | 13 |
| Smoothness | 11 | 12 | 12 | 12 | 12 | 13 |
| Running of a comb | 12 | 12 | 12 | 12 | 12 | 12 |
| After use: | | | | | | |
| Soft | 11 | 10 | 12 | 12 | 11 | 12 |
| Smoothness | 11 | 11 | 12 | 12 | 12 | 11 |
| Absence of stickiness | 12 | 12 | 11 | 12 | 11 | 11 |
| Running of a comb | 11 | 10 | 10 | 10 | 11 | 10 |
| Gloss | 13 | 13 | 13 | 13 | 13 | 13 |
| Taste | 13 | 13 | 13 | 13 | 13 | 13 |

[b]The numbers correspond to sample numbers of alkenylsuccinic acid esters of sugars

EXAMPLE 28

A conditioning rinse shown in Table 20 was prepared by using 6 alkenylsuccinic acid esters of sugars of the sample No. 2, 4, 6, 8, 10 and 12. For comparison, a rinse of the composition B containing no alkenylsuccinic acid esters of sugars was also prepared.

TABLE 20

| Composition | Amount of formulation (% by weight) | |
|---|---|---|
| | A | B |
| Stearyltrimethylammonium chloride | 1.0 | 1.5 |
| Alkenylsuccinic acid ester of sugar | 1.0 | 0 |
| Cetanol | 2.0 | 2.0 |
| Tsubaki oil | 1.0 | 1.0 |
| Lanolin fatty acid | 1.0 | 1.0 |
| Propylene glycol | 6.0 | 6.0 |
| Polyoxyethylene stearyl ether | 1.0 | 1.0 |
| Perfume | 0.3 | 0.3 |
| Purified water | balance | balance |

The rinse was used by 15 female subjects for evaluation of the performance. The results are shown in Table 21. The value in Table 21 shows the remainder when the number of persons who judged that B is better was subtracted from the number of persons who judged that A is better.

TABLE 21

| Item | Rinse[b] | | | | | |
|---|---|---|---|---|---|---|
| | 2 | 4 | 6 | 8 | 10 | 12 |
| At use: | | | | | | |
| Sliminess | 12 | 12 | 12 | 13 | 12 | 13 |
| Smoothness | 11 | 11 | 12 | 12 | 12 | 11 |
| Running of a comb | 12 | 11 | 11 | 12 | 11 | 12 |
| After use: | | | | | | |
| Soft | 12 | 12 | 12 | 12 | 12 | 13 |
| Smoothness | 11 | 11 | 12 | 11 | 12 | 12 |
| Absence of stickiness | 12 | 11 | 12 | 11 | 12 | 11 |
| Running of a comb | 11 | 12 | 12 | 11 | 12 | 12 |
| Gloss | 13 | 13 | 13 | 13 | 13 | 13 |
| Taste | 13 | 13 | 13 | 13 | 13 | 13 |

[b]The numbers correspond to sample numbers of alkenylsuccinic acid esters of sugars

EXAMPLE 29

A cleansing cream of the composition of Table 22 was prepared by using alkenylsuccinic acid esters of sugars of the sample No. 1 to 14.

TABLE 22

| Composition | Amount of formulation (% by weight) |
|---|---|
| Beeswax | 3 |
| Solid paraffin | 10 |
| Vaseline | 15 |
| Liquid paraffin | 40 |
| Sorbitan sesquiolate | 3 |
| polyoxyethylene sorbitan monoolate | 1 |
| Alkenylsuccinic acid ester of sugar | 5 |
| Perfume, Antioxidant, Antiseptic | trace |
| Purified water | balance |

It was recognized that the cleansing cream into which the alkenylsuccinic acid ester of a sugar of the present invention was formulated was superior to cream containing no ester of the present invention in spread and oiliness at use.

EXAMPLE 30

A neutral cream of the composition of Table 23 was prepared by using alkenylsuccinic acid esters of sugars of the sample No. 1 to 14.

TABLE 23

| Composition | Amount of formulation (% by weight) |
|---|---|
| Liquid paraffin | 10 |
| Vaseline | 10 |
| Glycerin monostearate | 0.5 |
| Isopropyl palmitate | 2 |
| Glycerin | 3 |
| Alkenylsuccinic acid ester of sugar | 4 |
| Perfume, Antioxidant, Antiseptic | trace |
| Purified water | balance |

The neutral cream into which the alkenylsuccinic acid ester of a sugar of the present invention was formulated was superior to cream containing no ester of the present invention in smoothness and moistness. Further, the effect was sustained for a long period of time.

EXAMPLE 31

Toothpaste of the composition of Table 24 was prepared by using alkenylsuccinic acid esters of sugars of the sample No. 1, 3, 5 and 7.

TABLE 24

| Composition | Amount of formulation (% by weight) |
|---|---|
| Calcium carbonate | 39.0 |
| Sorbitol | 22.0 |
| Sodium carboxymethyl cellulose | 1.1 |
| Sodium lauryl sulfate | 1.3 |
| Saccharin | 0.1 |
| Alkenylsuccinic acid ester of sugar | 0.5 |
| Ethyl para-hydroxybenzoate | 0.01 |
| Perfume | 1.0 |
| Purified water | balance |

It was recognized that the toothpaste into which the alkenylsuccinic acid ester of a sugar of the present invention was formulated was superior to toothpaste containing no ester of the present invention in the cleaning effect and a feeling at the use.

What is claimed is:

1. A cosmetic composition comprising an alkenylsuccinic acid half ester formed by esterifying a saccharide with an alkenylsuccinic anhydride in an amount of at least 30 parts by weight based on 100 parts by weight of the saccharide, and a cosmetic carrier, wherein the saccharide is selected from the group consisting of an amino sugar, a sugar alcohol, and a reduced starch.

2. A cosmetic composition according to claim 1, wherein the alkenylsuccinic acid half ester is a $C_{2-20}$ alkenyl-succinic acid ester.

3. A cosmetic composition according to claim 1, wherein the the amount of alkenylsuccinic anhydride is from 30 to 150 parts by weight based on 100 parts by weight of the saccharide.

4. A cosmetic composition according to claim 1, wherein the alkenylsuccinic acid half ester is in the form of a reaction mixture resulting from the reaction of the alkenylsuccinic anhydride and the saccharide in the presence of an alkali catalyst.

5. A cosmetic composition according to claim 1, wherein the carrier is a carrier for a hair care composition, and which contains the ester in an amount of 0.1 to 15% by weight based on the composition.

6. A cosmetic composition according to claim 1, wherein the carrier is a carrier for a skin care composition and contains the ester in an amount of 0.5 to 30% by weight based on the composition.

7. A process for producing an alkenylsuccinic acid half ester of a saccharide, which comprises esterifying the saccharide with an alkenylsuccinic anhydride in an amount of at least 30 parts by weight based on 100 parts by weight of the saccharide in the presence of an alkali catalyst, wherein the saccharide is selected from the group consisting of an amino sugar, a sugar alcohol, and a reduced starch.

8. A method for producing a cosmetic composition which comprises admixing an alkenylsuccinic acid half ester formed by esterifying a saccharide with an alkenylsuccinic anhydride in an amount of at least 30 parts by weight based on 100 parts by weight of the saccharide, with a cosmetic carrier, wherein the saccharide is selected from the group consisting of an amino sugar, a sugar alcohol, and a reduced starch.

9. A method according to claim 8, wherein the alkenylsuccinic acid half ester is in the form of a reaction mixture resulting from the reaction of the saccharide and the alkenylsuccinic anhydride in an amount of 30 to 150 parts by weight based on 100 parts by weight of the saccharide in the presence of an alkali catalyst.

* * * * *